(12) United States Patent
Heaton et al.

(10) Patent No.: US 6,814,079 B2
(45) Date of Patent: *Nov. 9, 2004

(54) SURGICAL DRAPE AND SUCTION HEAD FOR WOUND TREATMENT

(75) Inventors: Keith Patrick Heaton, Poole (GB); Kenneth William Hunt, Wimborne (GB)

(73) Assignee: KCI Licensing, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/366,227

(22) Filed: Feb. 13, 2003

(65) Prior Publication Data

US 2003/0188754 A1 Oct. 9, 2003

Related U.S. Application Data

(63) Continuation of application No. 09/835,500, filed on Apr. 16, 2001, now Pat. No. 6,553,998, which is a continuation of application No. 09/350,581, which is a continuation of application No. PCT/GB98/02713, filed on Sep. 9, 1998, now Pat. No. 6,345,623.

(30) Foreign Application Priority Data

Sep. 12, 1997 (GB) .............................. 9719520

(51) Int. Cl.$^7$ .............................................. A61B 19/00
(52) U.S. Cl. ...................................... 128/897; 602/42
(58) Field of Search ............... 128/887–98; 602/42–53; 604/317–321, 327–328, 332, 355, 540, 541, 543

(56) References Cited

U.S. PATENT DOCUMENTS 6,345,623 B1 * 2/2002 Heaton et al. .............. 128/897
6,553,998 B2 * 4/2003 Heaton et al. .............. 128/897

* cited by examiner

Primary Examiner—John P. Lacyk

(57) ABSTRACT

A wound therapy combination comprising a suction head and a surgical drape. The suction head comprises a planar flange portion and a tubular connector piece on a first face that communicates with an aperture extending to a second face. The second face is formed with projections that define flow channels for facilitating flow of liquids to the aperture.

11 Claims, 4 Drawing Sheets

SURGICAL DRAPE AND SUCTION HEAD FOR WOUND TREATMENT

RELATED APPLICATIONS

This application is a continuation of U.S. application, Ser. No. 09/835,500 filed Apr. 16, 2001 now U.S. Pat. No. 6,553,998, which is a continuation of Ser. No. 09/350,581, filed on Jul. 9, 1999, now U.S. Pat. No. 6,345,623, which is a continuation, under 35 U.S.C. §120 of PCT international application number PCT/GB98/02713 filed Sep. 9, 1998 and designating the United States, which claims priority to Great Britain patent application No. 9719520.0 filed Sep. 12, 1997. By this reference, the full disclosure of U.S. application Ser. No. 09/350,581, PCT international application No. PCT/GB98/02713, and Great Britain patent application No. 9719520.0 are incorporated herein as though fully set forth in their respective entirety.

FIELD OF THE INVENTION

This invention relates to surgical drapes and suction heads for wound treatment.

BACKGROUND OF THE INVENTION

Surgical drapes are widely used in surgical operations for the purpose of reducing infection and facilitating the handling of skin around incisions. Normally, they are transparent or translucent. Typically, they consist of a flexible, plastic film which is adhesive-coated and which is applied to the area of the operation, prior to making the incision. Surgical drapes are also used for attaching treatment devices to patients after an operation, such as catheters or drainage tubes.

A further, recently developed use is for connecting a suction tube to a wound for the purpose of stimulating healing of the wound. Such use is described in our earlier applications Nos. WO 96/05873 and WO 97/18007.

Various proposals have been made in the past to design the surgical drape so that handling of the sticky, flexible, plastic film is facilitated. For example, U.S. Pat. No. 5,437,622 describes a surgical drape which is a laminate of three materials. The first material comprises a transparent, thin plastic film which is adhesive-coated and the adhesive face protected with a layer of release-coated paper. The other face of the adhesive-coated film is strengthened with a reinforcing layer of a less flexible, plastic film. Handling bars or strips are attached to the flexible, plastic film at its lateral edge to facilitate handling of the flexible, plastic film after stripping away the protective releasable layer.

Where is it is desirable to use a surgical drape primarily to attach a device such a s a catheter to a wound area after an operation or for long term treatment, it is inconvenient for the surgeon or nurse to have to adapt a standard surgical drape for this purpose. It would be more convenient to have a surgical drape which was suitable without adaptation to accommodate the treatment device.

SUMMARY OF THE INVENTION

One aspect of the present invention is directed to a solution to this problem. A second aspect provides a combined surgical drape and suction head for applying suction to a wound area to facilitate application of negative pressure therapy.

According to one aspect of the present invention there is provided a surgical drape which comprises a thin, flexible, adhesive-coated plastic film and a strengthening layer applied to the face opposite to the adhesive coating, the strengthening layer being a plastic film which is thicker or less flexible than said adhesive-coated film, and a protective, releasable layer applied to the adhesive coating, the drape having an aperture through at least the strengthening and adhesive coated film to permit, in use, access to a wound area, a first edge of the drape having non-adhesive coated handling bars for separating the adhesive-coated film from the protective layer, and wherein the protective layer comprises a separate strip extending parallel to the first edge of the drape, and which protects the adhesive coating in the region of the aperture and carries a flap overlapping the adjacent portion of the protective layer, said flap constituting a handle for facilitating removal of said strip prior to use. Preferably, non-adhesive coated handling bars are positioned at opposite lateral edges of the drape.

In practice, surgical drapes may be manufactured by laminating an adhesive-coated flexible film, such as a polyurethane film, to a protective releasable layer, such as a siliconized paper. A strengthening layer of thicker plastic material, e.g. a polyolefin such a polyethylene, may be applied to the non-adhesive coated face of the flexible film, so that a three-layer laminate is produced. These laminates are produced in substantial width and may be slit longitudinally to the desired width and then laterally to form drapes of the desired size.

After slitting to a desired width, handling bars are normally applied to the adhesive-coated layers at one or both lateral edges to facilitate separation of the film from the protective, releasable layer. While an aperture could be cut at the desired position through the layers to accommodate a catheter or a device such as those described in our above-mentioned applications, it is difficult to handle the highly pliable and adhesive film after the releasable layer has been stripped off.

Although the strengthening layer does somewhat improve the handling characteristics, this is not a complete answer to the problem. However, the handling characteristics are substantially improved by providing a protective layer which is in at least two portions, one of which is in the form of a strip, e.g. one extending parallel to the lateral edges of the drape, and covering the peripheral area around the aperture through the drape. By providing a flap on this portion of the releasable layer, it can be stripped off initially so that the drape is first positioned around the device which is to pass through the aperture, and then the remaining part of the protective releasable layer is stripped off to adhere the drape to the patient's skin around the area to be treated.

In a preferred form of the invention in which negative pressure therapy is applied to a wound area, the surgical drape described above is combined with a suction head having a connector piece which is adapted to be connected to a suction tube. Thus, in this embodiment, the suction head can be adhered to the patient's skin in the area of the wound after removing the strip of protective releasable layer, and then the remaining part of the drape affixed to the patient's skin. In this way, the suction head is held firmly in place and, at the same time, seals the suction head to the wound area and prevents leakage of air from atmosphere into the wound area.

The invention also includes a suction head having a design which facilitates the suction of fluid from a wound area.

According to a further feature of the invention, therefore, there is provided a suction head for applying suction to a wound area which comprises a generally planar flange portion and a tubular connector piece on a first face, for connecting a suction tube to an aperture through the flange portion to the other face, said other face having projections defining flow channels facilitating flow of fluid towards said aperture.

Preferably, the suction head described above is combined with a surgical drape, the drape comprising a thin, flexible, adhesive-coated plastic film, and the tubular connector piece extends through an opening in the plastic film with the adhesive coating adhered to said first face of the flange portion.

Preferably, the suction head is used in conjunction with an open-celled foam pad so that one surface of the foam pad is placed in contact with a wound area and the suction head applied to the other surface of the foam pad. In the case of deep wounds the foam may be shaped and placed so that it is packed into the wound cavity as described in our above-cited PCT applications. According to another technique, which is particularly applicable to superficial wounds, the foam pad may be a relatively thin pad which is placed over the wound. The suction head is placed in contact with the open face of the foam pad and the drape applied over the suction head to fix the assembly to the patient's skin.

Various types of open celled foams can be used as described in our above-cited PCT applications. The foam may be a polyurethane foam but polyvinyl acetate (PVA) foams are preferred, especially when used as a pad which placed over the wound. These are to some extent hydrophilic, which seems to exhibit beneficial comfort properties when applied to the skin. Wound healing is stimulated by maintenance of moist conditions in the wound area, and this is facilitated by using a hydrophilic foam.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
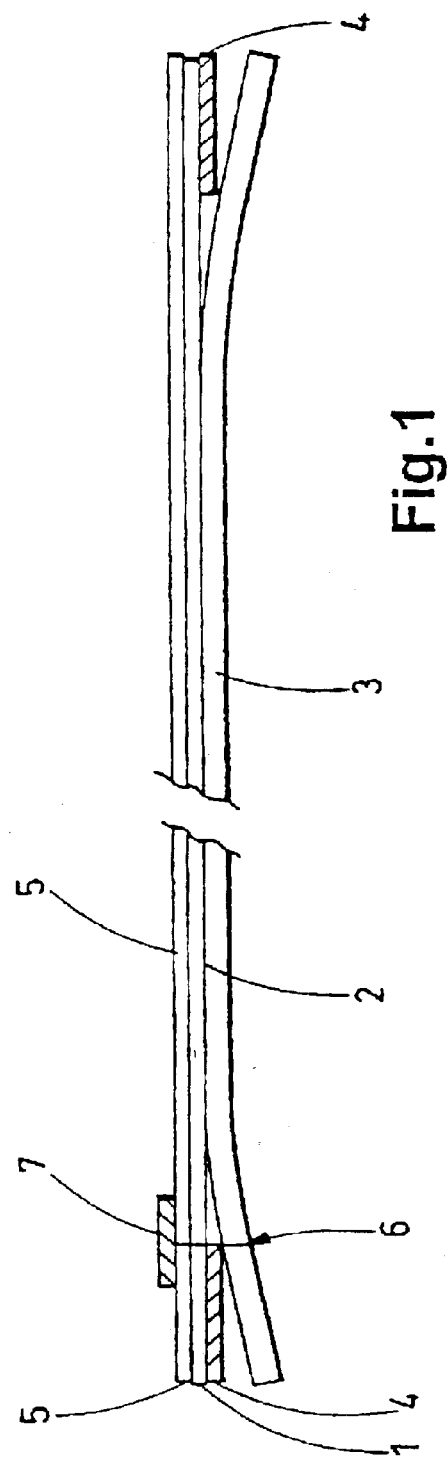
FIG. 1 represents a conventional design of surgical drape.
Figure 2:
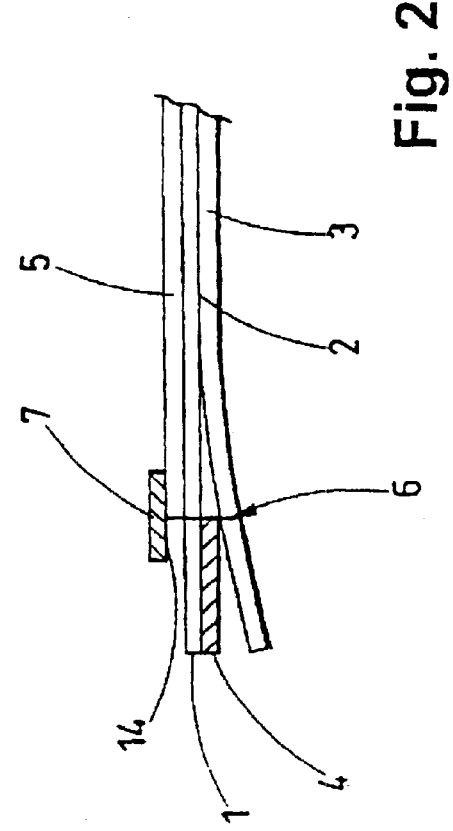
FIG. 2 represents a variation in the design of the handling bars at one end of the drape shown in FIG. 1.

Referring to FIGS. 1 and 2 of the accompanying drawings, a conventional laminate for use as a surgical drape comprises a thin, flexible, transparent film 1 which is adhesive-coated on one face 2, normally with a high-tack pressure-sensitive adhesive, and is protected with a releasable layer 3. The thin plastic film is conveniently of polyurethane because is transmits moisture. Layer 3 is normally considerably thicker than film 1 and is coated on the surface adjacent to the adhesive with a releasable material such as a silicone to facilitate stripping away from the adhesive-coated film.

In order to facilitate removal of the adhesive-coated film prior to use of the device, handling bars 4 are bonded at each end to the adhesive-coated film 1. Thus, by holding one of the bars 4, the protective layer 3 can be stripped off and the adhesive face applied to the skin of the patient. To facilitate handling of the thin, flexible film 1, a strengthening plastic film 5 is frequently applied to the free face of the plastic film 1. This is generally also transparent or translucent. Film 5 is preferably not bonded with adhesive to film 1, but may remain in contact by reason of electrostatic forces or because of close contact between the two conforming surfaces of film 1 and film 5.

Usually, the surgeon or nurse will wish to strip off the protective layer 5 after the film 1 has been correctly placed on the patient's skin, and this can be facilitated by making partial cuts 6 through the film 1 and 5, so that as the handling bar 4 is drawn upwards from the patient's skin, the adhesive film 1 remains adhered to the patient, while the patient, while the partial cuts 6 cause separation of the flexible film from the strengthening film 5. Strengthening bars 7 may be provided to hold the lateral edges of the strengthening film 5 and film 1 together with their main parts.

An alternative arrangement is shown in FIG. 2, in which the strengthening film 5 is provided with a separate overlapping handling bar 14, to facilitate its removal from the flexible film 1.

Further details of the make-up and manufacture of surgical drapes are given in U.S. Pat. No. 5,437,622 and European patent application no. 0161865 and the prior art referred to therein, by this reference, the full disclosure of U.S. Pat. No. 5,437,622 and European patent application no. 0161865 are incorporated herein as though each now set forth in its respective entirety.

Figure 3:
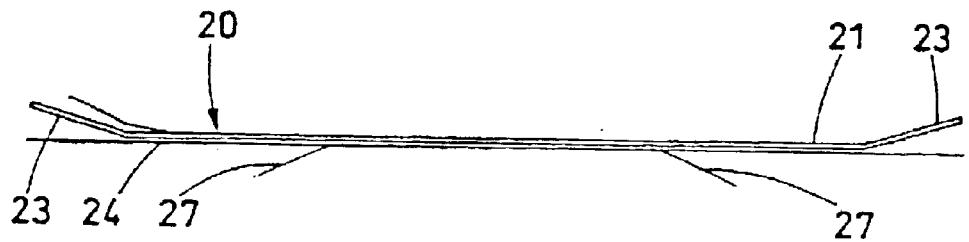
FIG. 3 is a view similar to FIG. 1 of a surgical drape in accordance with the invention.
Figure 4:
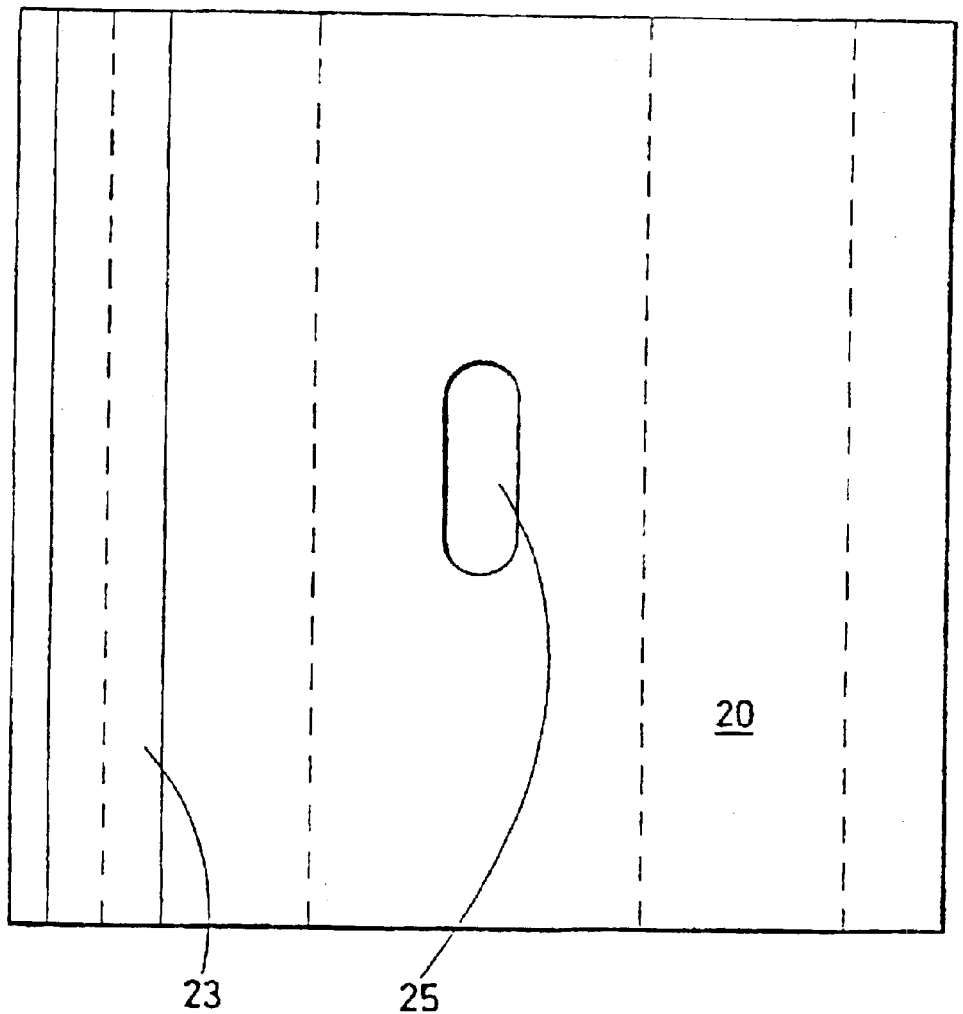
FIG. 4 is a plan view of the surgical drape shown in FIG. 3.

Referring to FIGS. 3 and 4, the surgical drape of the present invention comprises a protective outer film 20, laminated to a thin, flexible film 21. The flexible film includes an adhesive-coated layer which is protected with a release-coated sheet material 24. Lateral edges of the flexible film 21 are provided with handling bars 23. Thus far, the design is essentially the same as that shown in FIGS. 1 and 2.

The drape of the present invention differs from the drape shown in FIGS. 1 and 2 in that an aperture 25 is but through the strengthening layer 20 and through the flexible layer 21. The other difference compared with the prior art drapes is that the protective releasable layer is formed in at least two sections.

In the embodiments shown in FIGS. 3 and 4, the central portion of the releasable layer comprises a strip 26, having flaps 27 which overlap the remaining outboard portions of the releasable layer. The purpose of this is to enable the central strip 26 to be removed first, without disturbing the remaining portions of the releasable layer. The drape can then be fitted around the wound area and, if desired, a suction device or other treatment device passed through the aperture 25 and secured to the patient's skin with the peripheral areas of exposed adhesive coated film.

Figure 5:
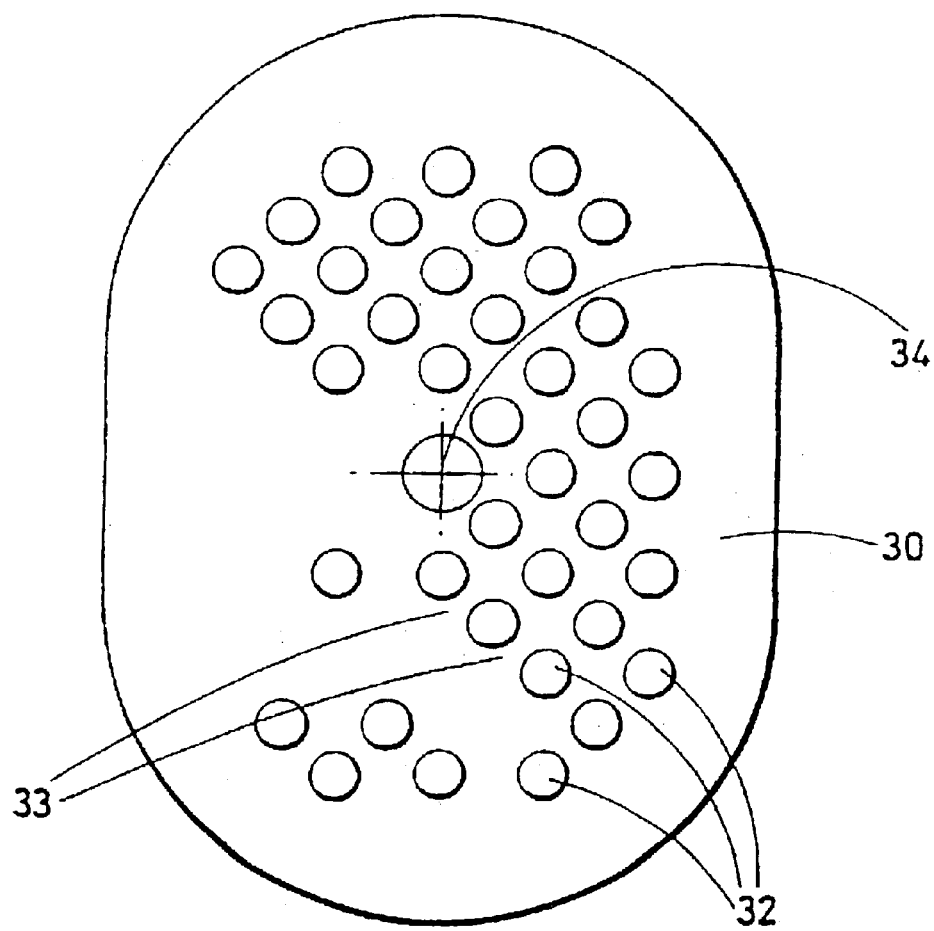
FIG. 5 is a plan view from beneath of a suction head in accordance with the invention.
Figure 6:
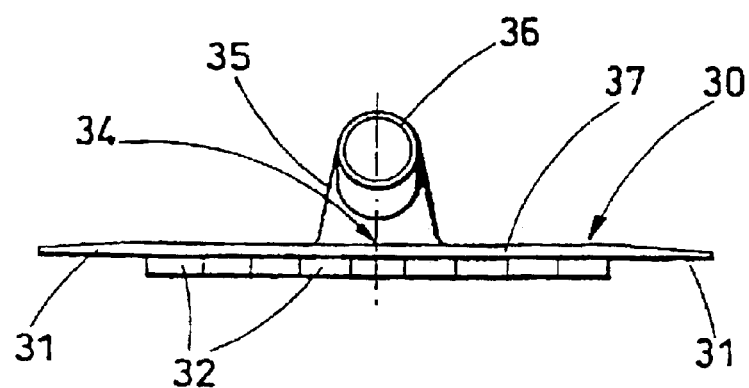
FIG. 6 is a side elevation of the suction head shown in FIG. 5.
Figure 7:
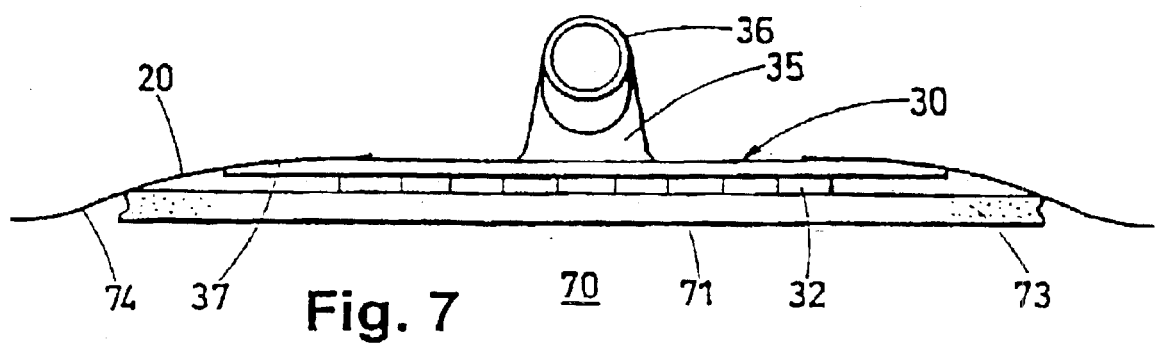
FIG. 7 is a view similar to FIG. 6 but shows the suction head secured to a skin surface with the drape and with a foam pad located between the head and the skin surface.

An example of a device for applying suction to the wound area is illustrated in FIGS. 5, 6, and 7.

Referring to these figures, the suction head comprises a flange portion 30 having a tapered edge 31, and a profile which may be of any desired shape but is generally rounded at its edges. On the face of the flange 30 intended for contact with the patient's skin or a foam pad are formed a series of projections 32 which are distributed over the surface of the flange apart from the peripheral edge portion 31. The purpose of these projections is to provide fluid channels 33 facilitating the flow of fluids form any point of the flange to a central point 34, from which it is intended to apply suction. The suction head includes a connector 35, located above the aperture 34, having a tubular end 36 adapted for receiving and connecting a catheter. The tubular and may have an outwardly tapered portion to facilitate feeding a catheter into the connector. The upper surface 37 of the suction head has a substantially smooth surface.

In use, the connector portion 35 is sized so that it extends through the aperture 25 in the surgical drape shown in FIGS. 3 and 4, with the adhesive surface around the aperture bonded to the smooth surface 37 of the flange 30. The suction head may be packaged in this condition with the surgical drape so that in use, the strip 26 is removed by pulling on the handles 27 thus exposing the adhesive surface in the vicinity of and surrounding the suction head. The suction head can then be fixed in the desired position on the patient's wound and then the remaining portion of the protective film removed to fix the drape to the patient. The flange 30 of the suction head may be somewhat oval as shown in FIG. 5, and have dimensions as indicated in this Figure, i.e. a longer dimension of about 95 mm and short dimension of about 70 mm. Alternatively, the flange may be circular and be smaller in plan view. For example, the diameter of a circular suction head may be from about 30 to 50 mm in diameter, e.g. about 40 mm. It has been found that the suction head flange should not overlap the area of the wound. Thus, in the case of smaller wounds a smaller head is indicated.

FIG. 7 shows the suction head attached to a wound area 71 of a patient 70. The suction head is pressed into firm contact with a flexible, open-celled foam 73, which is itself pressed into contact with a wound area 71. The suction head and foam pad are pressed into contact with the wound area by a surgical drape 20 having an adhesive surface 74. The adhesive surface is bonded to the patient's skin outside the periphery of the foam pad and suction head. It is also bonded to upper surface 37 of the suction head. An aperture is formed in the drape to permit the connector portion 35 to extend upwardly through the drape. In order to avert the danger of incorrect catheter tubes being fitted to the connector 35, the latter may have a customized cross-section or internal projection such as a rib or key which cooperates with a corresponding slot, or key way in the catheter. Alternatively, the catheter may be molded with a projection or longitudinal rib which operates with a corresponding slot or key way in the aperture of the connector 35.

The foam pad may be packaged in a plastic pouch, sterilized by gamma irradiation and supplied in the same box or in other packing units as the suction head and drape.

Figure 8:
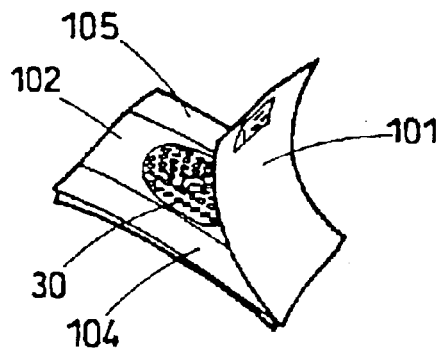
FIG. 8 is a perspective view of the drape with a central strip portion of the protective sheet in the course of being removed.
Figure 9A:
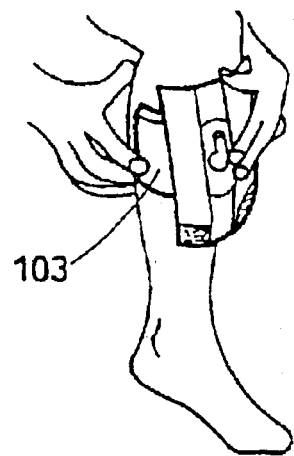
FIGS. 9a through 9c illustrate the steps of affixing the dressing assembly to a wound area on a patient's leg and attachment to a negative pressure assembly.
Figure 9B:
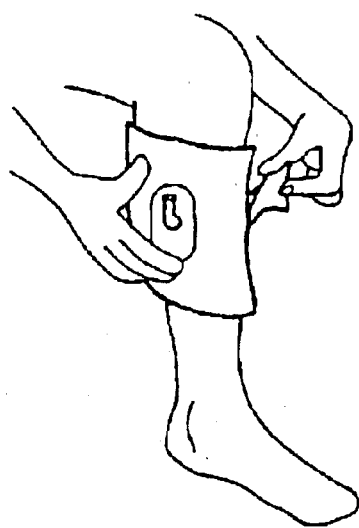
Figure 9C:
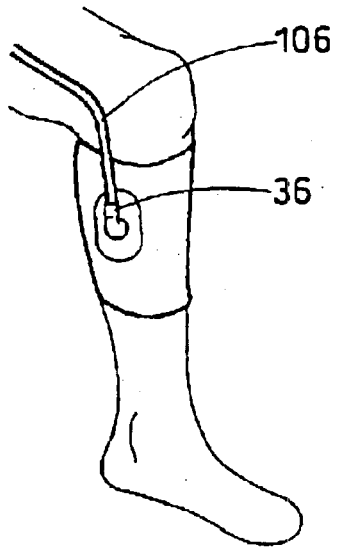

FIGS. 8, 9a, and 9b illustrate the way in which the drape-suction head combination is fitted to a wound on the patient's skin. In FIG. 8, a backing sheet 101 having a release coated surface is removed in the first step from the adhesive face 102 of the drape to expose the face of connector 30. A pad 103 of foam is positioned over the wound area and the drape placed over the foam pad, the drape being adhered to the skin above and below the pad (FIG. 9a). The lateral protective strips 104 and 105 are removed in turn from the drape and the assembly adhered to the skin (FIGS. 9b and 9c). Finally, spout 36 is connected to a tube 106 which is then connected to a source of suction, e.g. a pump as described in our above PCT application, in order to apply negative pressure to the wound. The suction head and drape assembly as shown in FIG. 8, with the smooth surface 37 adhered to the drape, is conveniently packaged in an easily openable plastic bag or pouch, and sterilized for immediate use.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. In any case, because the scope of the present invention is much broader than any particular embodiment, the foregoing detailed description should not be construed as a limitation of the scope of the present invention, which limited only by the claims appended hereto.

What is claimed is:

1. A wound therapy device for applying suction to a wound area, comprising:
   a suction head comprised of a plurality of channels for facilitating flow of fluids to an opening of said suction head, wherein said opening is adapted for connection to a suction tube; and wherein said channels are defined by a plurality of projections from said suction head, such that said projections are adapted to be in contact with a wound surface.

2. The wound therapy device of claim 1, further comprising a surgical drape having an aperture coincident said opening, said surgical drape extending over a region, and overlapping beyond the perimeter of said suction head, and wherein said surgical drape comprises a flexible adhesive coated film adhered to said region of said suction head and a release-coated backing extending over said suction head and adhered to the overlapping portion of said surgical drape.

3. The wound therapy device of claim 2, further comprising a source of suction.

4. The wound therapy device of claim 3, wherein said source of suction is a pump.

5. A wound therapy device, comprising:
   a suction head having a first face;
   a second face opposite said first face;
   an opening through said first face and through said second face; and
   a plurality of flow channels in fluid communication with said opening for facilitating flow of fluids to said opening.

6. The wound therapy device of claim 5 further comprising a surgical drape having an aperture coincident said opening, said surgical drape extending over a region of said first face, and overlapping beyond the perimeter of said first face.

7. The wound therapy device of claim 6 wherein said surgical drape comprises a flexible adhesive coated film adhered to said region of said first face and a release-coated backing extending over said second face and adhered to the overlapping portion of said surgical drape.

8. The wound therapy device of claim 7 further comprising a foam interposed between said second face and a wound.

9. The wound therapy device of claim 5 further comprising a source of suction in communication with said opening.

10. The wound therapy device of claim 9 wherein said source of suction is a pump.

11. The wound therapy device of claim 5 wherein said flow channels are defined by a plurality of projections from said second face.

* * * * *